United States Patent
Hehenberger

(10) Patent No.: US 6,534,006 B2
(45) Date of Patent: Mar. 18, 2003

(54) CHEMICAL INDICATOR FOR DETERMINING THE ADEQUACY OF A LIQUID STERILIZATION PROCESS

(75) Inventor: Rodney K. Hehenberger, Apple Valley, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/846,839

(22) Filed: Aug. 30, 2001

(65) Prior Publication Data

US 2002/0039792 A1 Apr. 4, 2002

Related U.S. Application Data

(63) Continuation-in-part of application No. 09/632,919, filed on Aug. 4, 2000, now abandoned.

(51) Int. Cl.[7] .............................................. G01N 31/22
(52) U.S. Cl. .......................... 422/58; 116/206; 422/55; 422/57; 436/1
(58) Field of Search .............................. 422/55, 56, 57, 422/58, 61; 436/1, 127, 128, 164; 116/206

(56) References Cited

U.S. PATENT DOCUMENTS

| | | | |
|---|---|---|---|
| 3,667,916 A | * | 6/1972 | Sliva et al. |
| 4,091,921 A | * | 5/1978 | Lewis |
| 4,138,216 A | | 2/1979 | Larson et al. |
| 4,382,063 A | * | 5/1983 | Romito et al. |
| 4,539,256 A | * | 9/1985 | Shipman |
| 4,565,783 A | * | 1/1986 | Hansen et al. |
| 4,613,544 A | * | 9/1986 | Burleigh |
| 4,726,989 A | * | 2/1988 | Mrozinski |
| 4,826,772 A | * | 5/1989 | Meathrel |
| 4,867,881 A | * | 9/1989 | Kinzer |
| 5,057,434 A | * | 10/1991 | Prusik et al. |
| 5,139,957 A | * | 8/1992 | Grack |
| 5,258,065 A | * | 11/1993 | Fujisawa |
| 5,260,360 A | * | 11/1993 | Mrozinski et al. |
| 5,352,513 A | * | 10/1994 | Mrozinski et al. |
| 5,366,872 A | * | 11/1994 | Hird et al. |
| 5,622,764 A | | 4/1997 | Battles |
| 5,723,308 A | * | 3/1998 | Mach et al. |
| 5,728,350 A | * | 3/1998 | Kinoshita et al. |
| 5,780,098 A | * | 7/1998 | Battles |
| 6,010,776 A | * | 1/2000 | Exsted et al. |
| 6,287,518 B1 | * | 9/2001 | Ignacio et al. |

FOREIGN PATENT DOCUMENTS

| JP | 401102360 A | * | 4/1989 |
|---|---|---|---|
| WO | WO 98/58683 | | 12/1998 |

OTHER PUBLICATIONS

Publication CIE No. 15 (E–1.3.1) 1971, Colorimetry: Uniform Colour Spaces, Colour Differences, Colour Difference Equations and Metric Colour Terms, Bureau Central de al CIE, Paris (1971).*
Chamberlin, GJ and DG Chamberlin, Colour: Its Measurement, Computation and Application, Heyden and Son, pp. 3–8, 37, 46, 48–49, 54 (1980).*

(List continued on next page.)

Primary Examiner—Jan Ludlow
(74) Attorney, Agent, or Firm—John A. Burtis

(57) ABSTRACT

A sterilization indicator that presents a visually distinct and uniform color transition after having been passed through sterilizing conditions. This sterilization indicator has a base layer with an indicator compound applied to at least an indicating region thereon. It also has a raised lamina attached to the base layer so as to substantially surround the indicating region.

5 Claims, 1 Drawing Sheet

OTHER PUBLICATIONS

Judd, DB, MacAdam, DL and G Wyszecki Spectral Distribution of Typical Daylight as a Function of Correlated Color Temperature, *J. Opt. Soc. Am.* 54 (8) pp. 1031–1040 (1964).*

Guild, J. The Colorimetric Properties of the Spectrum, *Phil. Trans. Roy. Soc. A* 230, pp. 149–187 (1931).*

Wright, WD, A Redetermination of the Trichromatic Coefficients of the Spectral Colours, *Trans. Opt. Soc.*, 29, pp. 225–243 (1927).*

Billmeyer, FW and M Salzman, Principles of Color Technology, $2^{nd}$ Edition, Wiley, pp. 40–41 (1981).*

Agoston, GA, Color Theory and Its Application in Art and Design, ed. by DL MacAdam, Springer–Verlag, pp. 48–58, 90–91, 193–194 (1987).*

Berger–Schum, A. Practical Color Measurement: A Primer for the Beginner, a Reminder for the Expert, translated by M Saltzman, Wiley, pp. 20, 26–33, 55–56 (1994).

Supplement 2 to Publication CIE No. 15 (EI.3.1) Uniform Color Spaces, Color Difference Equations, Psychometric Color Terms, Bureau Central de al CIE, Paris 10–12 (1971).

McDonald, R, Colour Physics for Industry, Dyers' Company Publications, pp. 111–113 (1987).

Hunt, RWG, *Measuring Colour*, Ellis Horwood Ltd., pp. 118–122 (1987).

ASTM E1 79–90, *Standard Terminology of Appearance, ASTM Committee E–12 on Appearance*, ASTM Standards on Color and Appearance Measurement, $3^{rd}$ edition, pp. 174–179, 731–737 (1991).

* cited by examiner

CHEMICAL INDICATOR FOR DETERMINING THE ADEQUACY OF A LIQUID STERILIZATION PROCESS

This application is a continuation-in-part of application Ser. No. 09/632,919, filed Aug. 4, 2000, now abandoned.

FIELD OF THE INVENTION

The invention relates generally to chemical indicators used to monitor the adequacy of a liquid sterilization process, and more specifically to chemical indicators that exhibit a uniform, easy to read color change when exposed to sterilizing conditions. An objective test for measuring color uniformity in chemical sterilization indicators is also described.

BACKGROUND OF THE INVENTION

A reliable supply of sterile instruments and supplies is vitally important to modern medical practice. Various types of apparatus are known for sterilizing reusable goods within a hospital setting. Perhaps the best known is the steam autoclave, which uses high temperature and high pressure steam to render medical goods sterile. Steam as a sterilizing gas is fast and effective, but requires high temperatures. Goods that cannot withstand autoclaving temperatures can be sterilized with sterilizers using biocidal gases such as ethylene oxide or hydrogen peroxide.

Alternatively, some types of medical goods are suited to being sterilized by a liquid bath. A commercial example of a liquid sterilization process utilizes the Steris™ System 1 Processor and Steris™ 20 sterilant (peracetic acid) available from the Steris Corporation of Mentor, Ohio.

Regardless of the method and sterilizing agent selected, an important part of the process of providing sterile goods is the verification that the sterilization has been effective. There are two broad classes of indicators that are used to make this verification. The first class includes biological indicators; these devices include viable spores of particularly hardy stains of bacteria. After the sterilizing cycle, the user places the biological indicator in an environment conducive to bacterial growth. If no growth occurs, it is presumed that the cycle was effective. The second class includes chemical indicators; these devices include a portion coated with a chemical such as an indicator ink which undergoes a visible change when subjected to the predetermined lethal environment that the sterilizer is designed to create within the sterilizing chamber. If the visible change occurs, an effective cycle is presumed.

Preferably, chemical indicators show a first color very uniformly across their indicating region up until the moment all the pathogens on the goods have been destroyed. At that point the indicating region would change all at once to a dramatically different, but still very uniform color. Practically, this is a very difficult objective to achieve, especially with a liquid sterilant. Optionally, the product may have a failsafe built in to provide early warning of sterilizer failure.

The art remains interested in ways to provide very distinct, uniform transitions particularly for liquid sterilization procedures. A chemical indicator for use with a liquid bath sterilization cycle is subjected to different design constraints than a chemical indicator for a vapor sterilant procedures such as steam or ethylene oxide.

A chemical indicator is commercially available for the Steris liquid peracetic acid sterilization process from the Steris Corporation of Mentor, Ohio. The indicator ink associated with the product, however, is very small and difficult to see and read.

A clearly visible, uniform final color after a successful sterilization cycle is particularly desirable. Medical practitioners prefer not to subjectively judge the degree of color change against a visual standard. This is due in part to inherent human variability and subjectivity, such as degrees of color blindness, and a desire to reduce the costs associated with personnel training.

The Commission Internationale de l'Elcairage (CIE) has defined a uniform and objective color measurement method. The method includes definitions of the following parameters:

a standard illuminant;

a standard observer; and a uniform color space.

The standard illuminant does not refer solely to the light (which may be called the "source") but also includes a definition for the surrounding environment and the geometry of the measurement system. Four major types of illuminant are defined and named A, B, C, D and represent varying conditions of simulated incandescence or daylight. For general purposes, the de facto illumination is the standard illuminant 'A.'

The CIE also defines a standard observer, intended to represent the color perception of the average human viewer of a sample under the standard illuminant. The CIE defines what are called the "tristimulus" values for the standard observer. Also necessary when describing human color interpretations is a definition on which area of the eye the color is impinging. The CIE defines the "2° standard observer," representing the central, most color-sensitive portion of the interior eye (called the fovea). It is understood that by combining the tristimuli in varying quantities, all colors can be numerically described as they would strike the fovea of a human eye.

The CIE also defines a uniform color space, represented in a chromaticity diagram called the CIE 1976 L*a*b* (CIELAB). The CIELAB chart describes colors along three axes:

L*: describing black to white on a scale of 0 to 100 a*: describing green to red b*: describing blue to yellow

This chromaticity diagram allows a directional difference between colors to be noted. A change of 1–2 CIELAB units is generally defined as the industrial tolerance. By definition, this means that a one unit change in any one of the L*, a* or b* measurements is considered visually discernible.

The CIE system provides a measurement system based on a shared color space. The CIELAB formulas, which are based on the best available approximations to a uniform color space, are used for many color-difference measurements.

Over the years, many companies and laboratories in a variety of fields have developed methods that allow them to specify their color tolerances and reproducibly evaluate them. Of these methods, there is one that is more precise and quite extensively employed. The method involves the use of a spectrophotometer. A spectrophotometer uses a tightly calibrated standard illuminant and measures the reflectance/transmittance of a sample across a broad spectrum of "visible" light (roughly 400–700 nm). Using the mathematical transformations developed by the CIE, the computer generates the L*a*b* values for the standard observer. This is a simple, yet very powerful tool for the evaluation of color samples.

SUMMARY OF THE INVENTION

The present invention provides a sterilization indicator that presents a visually distinct and uniform color transition after being subjected to a liquid sterilization procedure. The sterilization indicator has a base layer having an indicator compound associated with at least an indicating region thereof. The indicator also has a raised portion (preferably a lamina) attached to the base layer so as to substantially surround the indicating region. No theory is fully understood or advanced as to the precise reasons why the present invention is helpful with a liquid bath sterilization cycle. Surprisingly, a raised portion, conveniently in the form of an annulus around the indicating region, is helpful for use in a chemical indicator for monitoring a liquid peracetic acid sterilization cycle.

In another aspect, the invention provides an objective test for evaluating the uniformity of color in a chemical sterilization indicator.

DETAILED DESCRIPTION OF PREFERRED EMBODIMENTS

Figure 1:
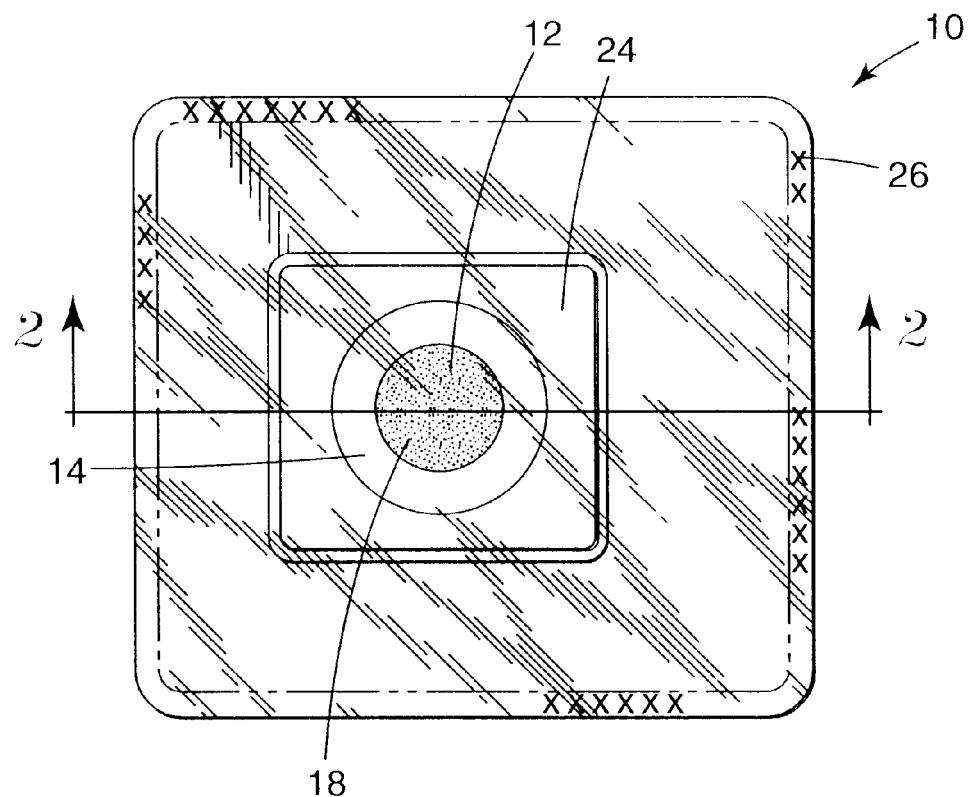
FIG. 1 is a top view of a sterilization indicator according to the present invention, particularly adapted to assess the efficacy of a liquid bath sterilization process.

Referring to FIG. 1, a top view of a sterilization indicator 10 according to the present invention is illustrated. The depicted embodiment is particularly adapted to assess the efficacy of a liquid bath sterilization process. A base layer 12 is provided, conveniently in the form of a circular disk. A raised portion (preferably a lamina) 14, conveniently in the form of a circular annulus, torus or doughnut is associated with (e.g., attached or laminated or adhered or printed) to the base layer 12 so as to define an indicating region 16 in the central portion of the base layer. An indicator compound or composition 18 is associated with (e.g., absorbed or coated onto) the base layer 12 at least within the indicating region 16.

The indicator compound or composition is chosen such that the compound or composition undergoes a distinct and generally permanent color change upon exposure to conditions that indicate the occurrence of sterilization. For a liquid sterilization process that employs a peracid (e.g., peracetic acid), the indicator composition typically will contain a colorant (or dye) and a halogen source. Suitable dyes include the sodium salt of fluorescein and phenol red. An indicator composition containing fluorescein, for instance, will turn from yellow to orange in the presence of a bromine source and a peracid and will turn from yellow to red in the presence of an iodine source. The indicator composition generally will contain between 0.5% and 10% of the dye by weight. The halogen source can be a halogen salt, such as an alkaline earth metal halide salt (e.g., magnesium bromide or magnesium chloride) or an alkali metal halide salt (e.g., potassium bromide). A sufficient quantity of the halogen source should be included in the indicator composition to react with a sufficient quantity of the dye to cause a color change at a desired rate. Typically, the indicator composition will contain between 1% and 60% of the halogen source by weight.

The indicator compositions may include a binder material or resin, such as a cellulose, or sodium acetate. They may also optionally include other ingredients such as colorants that do not change color during a sterilization process, resins that perform functions other than binding (e.g., providing water resistance or solvent dispersibility), and opacifying agents.

The base layer or substrate with which the indicating compound or composition is associated may be made of any material which provides the necessary support for the indicator compound or composition but does not substantially interfere with its indicative function. Suitable materials include, but are not limited to, natural and synthetic blotter papers and crepe papers and polyester films. The indicator compound or composition may be applied to the base substrate by any suitable method, including coating, printing or absorbing.

When the efficacy of a liquid bath sterilizing processes (e.g., an immersion in a solution of liquid peracetic acid such as is performed in the Steris System 1 Processor) is to be assessed, it is convenient to enclose the base layer 12 within a receptacle 20. The receptacle 20 conveniently includes a vapor permeable backing 22 and a cover 24 attached to the backing 22. Preferably, the vapor permeable backing 22 is constructed from a material, laminate or combination of materials that is permeable such that a vapor of the liquid sterilant may form within receptacle 20 and act on the compound 18.

Generally, materials suitable for the backing constructions will have pores that are of sufficient size and uniformity to provide an overall porosity and pore density that allows for suitable vapor transmission without significant leakage. For peracetic acid vapors, TYVEK brand spunbonded polyolefin film is considered preferred. Depending on the agent that needs to permeate the vapor permeable backing 22, other polymeric films may be used such as non-woven, microporous or microperforated films made of, for example, polytetrafluoroethylene, polyethylene, or polypropylene. It is believed that the vapor permeable backing may be constructed in accordance with the teaching of U.S. Pat. No. 4,539,256 (Shipman); U.S. Pat. No. 4,613,544 (Burleigh); U.S. Pat. No. 4,726,989 (Mrozinski); U.S. Pat. No. 4,867,881 (Kinzer); U.S. Pat. No. 5,260,360 (Mrozinski et al.); U.S. Pat. No. 5,352,513 (Mrozinski et al.); and U.S. Pat. No. 6,010,776 (Exsted), the entire contents of each of which are herein incorporated by reference. The backing layer may also be composed of more than one layer. For example, a microporous film can be laminated to a non-woven material to form a laminate backing material construction.

A cover 24 typically encloses indicating region 16. It is preferred that at least a portion of the cover be transparent so that the indicating region can be visually assessed without disassembling the receptacle 20. The cover may be made of any available material that provide a desired level of clarity and rigidity for a given application. Useful materials include polyesters such as polyester terephthalate, polyolefin materials such as polyethylene and polypropylene. Blends and/or co-polymers of such materials may also be used. The cover may be conveniently fabricated by vacu-forming or thermo-forming from a sheet of a suitable polymer such as polyester terephthalate. The cover may also be molded or extruded, and can include one or more additives such a hindered amine light stabilizer (HALS) compound.

Printing may also be provided, if desired, directly on the cover 24. It may be generally considered preferred to provide printing directly on the border portions of the cover to avoid interference of the ink and/or printing processes on the porosity of the backing material. Certain of the cover materials may be made receptive to printing by either or both surface treating the cover and using adhesive ink materials. The most useful surface treatment is a corona treatment, typically at levels between about 0.25 and 3.0 J/cm$^2$ in an air atmosphere. Useful adhesive ink formulations will typically include: an ink (black or colored); an extender resin (such as 3M Extender 7952 resin, available from 3M Company of Saint Paul, Minn.); an adhesive resin (such as acylate, cellulose acetate, shellac, urethane and chlorinated polyolefin resins); and, if necessary, one or more viscosity modifiers (such as carbitol acetate).

The backing 22 and cover 24 are attached together with suitable means. For example, they may be bonded together to form the receptacle 20 by thermo-bonding, indicated as bonded region 26. Alternatively, they may be adhesively adhered together. The bond 26 is preferably substantially liquid impermeable.

Preferably, cover 24 is substantially liquid impermeable to better control the exposure of the receptacle to the sterilant vapors (e.g., to restrict them to only those that permeate through layer 22). However, the sterilization indicator 10 may be constructed with a cover 24 that is slightly liquid or vapor permeable.

Figure 2:
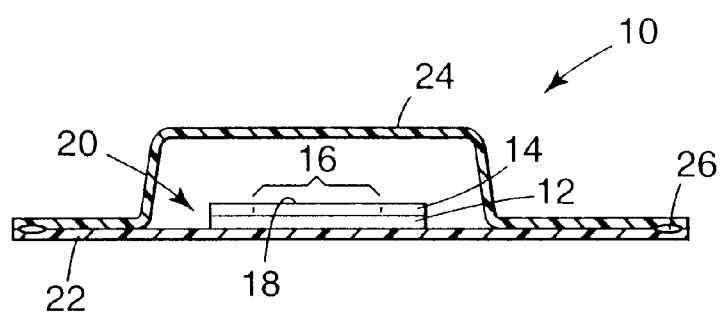
FIG. 2 is a cross-section side view taken along section lines 2—2 in FIG. 1.

Referring to FIG. 2, a cross-section view of the sterilization indicator 10 is illustrated. As shown, raised portion (e.g., lamina) 14 rises up above the level of the indicating compound 18 on base layer 12. In various embodiments of the present invention, the raised portion may be an ink printed on base layer 12, or another element adhered to the base layer 12 (as described in greater detail below).

EXAMPLES

Example 1

A Chemical Indicator for Peracetic Acid as a Comparative Example

To demonstrate the improvement in uniformity achieved by the invention, an example without a raised portion (e.g., 14) was prepared. This Example includes an indicator ink prepared in accordance with copending and coassigned U.S. patent application Ser. No. 09/019,341, filed Feb. 5, 1998, now U.S. Pat. No. 6,287,518 which is hereby incorporated herein by reference.

A base layer 12 was prepared by laminating a layer of filter paper to a polymeric film. The filter paper used in this lamination is commercially available as SS-410 from Schleicher & Schuell of New Hampshire. The polymeric film used in this lamination is a ethylene/methacrylic acid ionomer resin commercially available under the "Surlyn" trade name from E. I. Dupont de Nemours of Wilmington, Del. The thickness of the finished lamination was 0.040" (1.5 mm).

An indicating compound suitable for detecting the presence of peracetic acid vapor was prepared by mixing 10 grams of potassium bromide, 40 grams of sodium acetate, and 0.43 grams of Phenol Red (in the form of the sodium salt) in 500 grams of water. These ingredients are commercially available from Aldrich of St. Louis, Mo. The solution was mixed with at room temperature with a magnetic stir bar until all solids were visually dissolved. The solution had a cranberry color when complete, and was stored in a glass jar in a dark cabinet until used.

Approximately 150 mL of the solution of indicating compound was poured into an aluminum tray. Pieces of the paper/film laminate were then dipped, paper side down, in the solution for 30 seconds. Each coated piece was then placed between sheets of PET and squeegeed with a hand roller under moderate pressure. The coated pieces were then placed in dark oven at 52° C. for 20 minutes to dry. These dried, coated pieces then received a coating of acrylate-type adhesive, commercially available as VHB™ adhesive from 3M Company of St. Paul, Minn., applied by hand on the film side. Circular disks of 19 mm in diameter were cut from the pieces with a hand tool.

These disks were hand laminated to a vapor permeable backing. The backing is commercially available from Perfecseal of Philidelphia, Pa., and made of a layer of their SBP200 heat seal adhesive coated on a layer of spunbonded polyolefin film, in turn available as Tyvek™ 1073B from Dupont. Also obtained from Perfecseal were transparent covers prepared by vacu-forming a 15 mil (0.38 mm) thick film of PETG.

Receptacles were then formed by bonding the covers to the heat-seal adhesive on the vapor permeable backing so as to enclose the disks. A Vertrod Thermal Impulse Sealer Model 14P, commercially available from Vertrod Corporation of Brooklyn, N.Y., was used to form heat seals, the settings on the instrument being set to dwell=9.5 and heat= 9.5. Four heat seals were made along the four edges of the cover so as to render the receptacle liquid-tight.

These disks did not include a raised portion to illustrate the advantages of the present invention set forth in greater detail below.

Example 2

An Alternate Comparative Example

A second comparative example was prepared. The procedure of Example 1 was followed, except that after the laminate was dipped and dried, but before the VHB adhesive was applied, the pieces of laminate were inserted into a 4000TN LaserJet printer equipped with a model C4127X black ink cartridge, both commercially available from Hewlett-Packard of Palo Alto, Calif. Under computer control, an annular ring of black ink was applied to the surface of the laminate bearing the indicating compound. The annulus of ink had an outside diameter of 19 mm and an inside diameter of 13 mm. The disks that were then cut from the laminate corresponded to the outside diameter of the inked region.

Example 3

An Experimental Example

The procedure of Example 1 was followed, except that after the laminate was dipped and dried, an additional layer of the paper/film laminate was adhered using the VHB adhesive over the top of the layer that had been dipped. This top layer had holes of 13 mm punched in it prior to being applied, so that windows of indicating compound showed through the holes. Disks of 19 mm in outside diameter were cut from this double laminate so that the 13 mm window was concentric with the outside of the disk. This additional layer therefore forms a torus (e.g., doughnut) shaped raised lamina surrounding the indicating region. This assembly was then adhered with an acrylic transfer adhesive to the vapor permeable backing and the receptacle formed in the manner described above in Example 1.

The raised portion in this Example is a lamination. It could be a single layer of added material, or indeed the disk could be all of one material with a raised lip extending above the level of the indicating compound and still be within the scope of the invention. The thickness of the raised lamina in this Example is about 1.5 mm, but thicknesses between about 0.25 mm and 2.5 mm are believed to be suitable.

Example 4

Exposure to Sterilizing Conditions and Assessment

Three lots of each of the chemical indicators according to Examples 1–3 were prepared. Some of these samples were then run in the STERIS SYSTEM 1 Processor under full sterilization cycle conditions (i.e., they were believed exposed to a lethal cycle), attached to the interior of the sterilizer with a clip. All were inspected visually, and three samples from each lot were selected at random for instrument assessment. Since one of the goals is a very uniform color after sterilization, the samples were measured spectrophotometrically to determine the maximum difference between the color of the exposed indicating compound at any two points. Since it had been generally observed in other samples that the center of the disk had been the last to alter its color completely, the difference in color (in CIELAB terms) between the center point of a sample and a point 3 mm from the center towards the periphery was assessed.

To perform the assessment, an Xrite SP68S spectrophotometer, commercially available from Xrite, Inc. of Grandville, Mich., was used to measure the $\Delta E$ of the target spots. The $\Delta E$ is defined as the $(\Delta L^{*2}+\Delta a^{*2}+\Delta b^{*2})^{1/2}$ (in CIELAB terms).

The assessment was conducted generally in accordance with the Commission Internationale de l'Elcairage (CIE) Publication No. 15 (E-1.3.1) 1971, Colorimetery: Uniform Colour Spaces, Colour Differences, Colour Difference Equations and Metric Colour Terms, Bureaus Central de al CIE, Paris (1971); Supplement 2 to Publication CIE No. 15 (E-1.1.3.1) Uniform Color Spaces, Color Difference Equations, Psychometric Color Terms, Bureau Central de al CIE, Paris 10–12 (1971); Chamberlin, G J and D G Chamberlin, Color: Its Measurement, Computation and Application, Heyden and Son, 3 (1980) the entire contents of each of which are herein incorporated by reference; and ASTM test method E1164.

The type of spectrophotometer, its settings and the specification of the components used are set forth in Table A below. The identified specifications are the settings used for all spectrophotometric testing included in this example.

TABLE A

ASTM 1164-91 References and Testing Specifications

| ASTM 1164-91 Sect. | Specification | Sterilization Indicator rationale |
| --- | --- | --- |
| 6.1.1 | Transmittance | The user interprets the sterilization indicator color transmitted to the eye |
| 6.1.2 | Spherical | Section 8.2.3 defines spherical use for matte finishes on planar samples |
|  | Regular inclusion | Inclusion of reflected wavelengths of light from source is akin to user's view |
| 6.1.3 | Wavelengths 360–750 nm | Literature states that human can "see" light in the range of approximately 400–700 nm |
|  | 10 nm interval | Tighter intervals than standard industrially-used spectrophotometers (most operate at 20 nm) |
|  | 10 nm band-pass | Equal to wavelength measurement interval as recommended by ASTM 1164-91 |
| 6.1.4 | White tile | Standard calibration reflectance factor uses a white tile to represent 100% reflectance |

TABLE A-continued

ASTM 1164-91 References and Testing Specifications

| ASTM 1164-91 Sect. | Specification | Sterilization Indicator rationale |
| --- | --- | --- |
| 6.1.5 | Illuminant A 2° Observer | Standard illuminant suggested by literature Most specific visually observable color distinction and most similar to conditions of user-reading of sterilization indicator |
| 6.1.6 | Special Req. | N/A |

The instrument was equipped with a 6 mm aperture, set for specular inclusion, illuminating the target with $D_{65}$ illumination for a 2° observer, to measure L*a*b*. The results in terms of $\Delta E$, reported as the average of the three assessed samples from each of the three lots of each of the three Examples are summarized in Table 1 below.

TABLE 1

|  | $\Delta E$, lot 1 | $\Delta E$, lot 2 | $\Delta E$, lot 3 |
| --- | --- | --- | --- |
| Example 1 (Comparative) | 38.07 | 35.95 | 14.56 |
| Example 2 (Comparative) | 23.32 | 36.99 | 16.55 |
| Example 3 | 3.42 | 4.25 | 2.29 |

For reasons that are not completely understood, the color uniformity of the first and second Examples were poorest. Surprisingly, the color uniformity of Example 3 was much better.

The uniformity of color change for Examples 1 and 2 were poorest from a customer's perspective as measured objectively by the above-identified test. It will readily be appreciated that the uniformity in the final color of fully exposed chemical indicators according to the present invention is excellent. The preferred $\Delta E$ values for assessing uniformity of color change are less than 10, more preferably less than 8, and most preferably less than 4.

Example 5

Exposure to Inadequate Sterilizing Conditions and Assessment

Improvement in the uniformity of the final color of a properly exposed chemical indicator, while very desirable, should not be achieved by sacrificing a strong, easily identified difference between indicators that have been through an adequate sterilizing cycle and indicators that have been through an inadequate sterilizing cycle. To verify that the use of a raised portion had not detracted appreciably from this consideration, samples from each of the three lots of each of the Example materials were also put through the STERIS SYSTEM 1 processor, but this time with a 25% reduction in recommended amount of active ingredient of STERIS 20 Sterilant Concentrate.

The samples were again assessed spectrophotometrically, but this time the comparison was not between two spots on the same indicator, but between the center spots on the devices from the same lots that had been fully and not fully sterilized. Whereas in Example 4 a small number was desirable to the user, indicating uniformity across a single device that had been exposed to an acceptable cycle, in this Example 5 a large number is desirable to a user, indicating a large, easy to see difference between devices that have been through accept or reject sterilizing cycles. The results are summarized in Table 2 below.

TABLE 2

|           | ΔE, lot 1 | ΔE, lot 2 | ΔE, lot 3 |
|-----------|-----------|-----------|-----------|
| Example 1 | 61.15     | 63.24     | 90.01     |
| Example 2 | 67.07     | 44.00     | 79.82     |
| Example 3 | 41.04     | 68.57     | 52.99     |

All of these values represent differences that are easily perceived by normal human vision.

Example 6

An Alternative Experimental Example

The procedure of Example 3 was followed, except that the vapor permeable backing is XMP-6052 3M Propore™ Fabric commercially available from 3M Company and the transparent covers prepared by vacu-forming were approximately 0.30 mm thick film of polypropylene. This indicator showed very uniform color change, that is, ΔE was less than 4.

Example 7

A Second Alternative Experimental Example

A base layer was prepared by the procedure of Example 1.

An indicating compound suitable for detecting the presence of peracetic acid vapor was prepared by mixing 1.53 grams phenol red (in the form of the sodium salt), 164 grams of sodium acetate, and 40 grams potassium bromide in 2000 grams of water. The solution was mixed at room temperature with a magnetic stir bar until all solids were visually dissolved. The solution had a cranberry color when complete as described in Example 1.

Rolls of the paper/film laminate (base layer) were dip coated with the paper side down in the solution for approximately 10 seconds. The coated roll was then sent through a dryer at 49° C. for 10 minutes.

Next the dry coated paper/film laminate was flexographically printed with a series of annular rings of black ink (commercially available as FGN 3561 from Colorcon Corp., West Point, Pa.) on the paper side. The annulus of ink had an outside diameter of 19 mm and an inside diameter of 13 mm.

Then the printed paper/film laminate was coated with an acrylate-type heat-seal adhesive, commercially available as VHB adhesive from 3M Company, which was applied to the Surlyn side.

Circular disks of 19 mm in diameter were cut from the laminate corresponding to the outside diameter of the inked region. The disks were laminated to the vapor permeable backing described in Example 1.

Receptacles were then formed by bonding the covers to the heat-seal adhesive on the vapor permeable backing so as to enclose the disks. A tray sealer was used to form heat seals along the four edges of the cover so as to render the receptacle liquid-tight.

This chemical indicator also exhibited uniform color change, that is, ΔE was less than 10.

Example 8

Experimental Example with a Printed Cover Member

The procedure of Example 6 was used to make chemical indicators with printed covers. It was difficult to get the ink to adhere to the cover since the material lacked polar functionality. Thus, before transparent covers were attached to the laminated base layer to form the receptacles, they were screen printed on the open side of the cover on the flange with the ink formulations listed in Table 3. The transparent covers were thermoformed from a 0.254 mm–0.381 mm thick film extruded from a random co-polymer of polypropylene/polyethylene resin commercially available as Amoco PP 8249 resin from BP Amoco, Chicago, Ill. The side to be printed was corona treated at 2.25 J/cm$^2$. Then, each of the ink formulations in Table 3 was printed on the open side of the cover using a 230 mesh flat bed screen. The ink was cured for 5 minutes at 66° C., and the cover was sealed to the base layer as described in Example 1. By printing on the open side of the cover the ink was not in contact with the sterilization solution that was being monitored.

TABLE 3

| Run Number | Composition | Amount (g) |
|------------|-------------|------------|
| 1 | 3M Process Black[1] | 40 |
|   | 3M Extender 7952[1] | 10 |
|   | Eastman 515-12 chlorinated polyolefin[2] | 5 |
|   | Carbitol acetate (viscosity reducer) | As needed |
| 2 | 3M Process Black[1] | 40 |
|   | 3M Extender 7952[1] | 10 |
|   | 3M R21509 urethane resin[1] | 5 |
|   | Carbitol acetate (viscosity reducer) | As needed |

[1]Available from 3M Company, St. Paul, MN
[2]Available from Eastman Chemical, Kingsport, TN The combination of corona treatment and the resins used to improve adhesion provided substantial bonding of the ink to the film of the cover.

I claim:

1. A sterilization indicator for a liquid sterilization procedure, comprising:
    a base layer having an indicator composition associated with an indicating region thereof, the indicator composition designed to change color when the sterilization indicator is placed in a liquid sterilization procedure;
    a raised portion attached to the base layer so as to substantially surround the indicating region; and
    a receptacle enclosing the base layer and the raised portion, the receptacle comprising:
        a vapor permeable backing, and
        a cover attached to the backing and having a transparent portion allowing visual inspection of the indicating region without removing the base layer from the receptacle.

2. The sterilization indicator according to claim 1 wherein the liquid sterilization procedure is liquid peracetic acid sterilization procedure.

3. The sterilization indicator according to claim 2 wherein the indicator composition comprises one or more dyes and one or more halogen sources.

4. The sterilization indicator according to claim 1 wherein the raised portion is a lamina that entirely surrounds the indication region, and further wherein the raised lamina is at least 0.25 mm in thickness.

5. The sterilization indicator according to claim 1 wherein the raised portion is an ink printed on the base layer such that the raised portion does not change color when the sterilization indicator is exposed to the sterilization procedure.

* * * * *

UNITED STATES PATENT AND TRADEMARK OFFICE
CERTIFICATE OF CORRECTION

PATENT NO.   : 6,534,006 B2
DATED        : March 18, 2003
INVENTOR(S)  : Hehenberger, Rodney K.

It is certified that error appears in the above-identified patent and that said Letters Patent is hereby corrected as shown below:

Column 1,
Line 41, replace "stains" with the word -- strains --;
Line 65, replace "procedures" with the word -- procedure --;

Column 4,
Line 17, replace "processes" with the word -- process --;
Line 53, replace "provide" with the word -- provides --;
Line 61, insert the word -- as -- following the word "such";

Column 5,
Line 8, replace "acylate" with the word -- acrylate --;
Line 60, delete the word "with" preceding the word "at";

Column 6,
Line 11, replace the word "Philidelphia" with the word -- Philadelphia --;

Column 7,
Line 32, replace the word "Colorimetery" with -- Colorimetry --;

Signed and Sealed this

Thirtieth Day of December, 2003

JAMES E. ROGAN
*Director of the United States Patent and Trademark Office*